US00PP29698P3

(12) United States Plant Patent
Kordes

(10) Patent No.: US PP29,698 P3
(45) Date of Patent: Sep. 25, 2018

(54) SHRUB ROSE PLANT NAMED 'KORTUBERLOU'

(50) Latin Name: *Rosa hybrida*
Varietal Denomination: KORtuberlou

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 6 days.

(21) Appl. No.: 15/330,132

(22) Filed: Aug. 12, 2016

(65) Prior Publication Data

US 2018/0049358 P1 Feb. 15, 2018

(51) Int. Cl.
*A01H 5/02* (2018.01)

(52) U.S. Cl.
USPC ..... Plt./102
CPC ..... *A01H 5/0222* (2013.01)

(58) Field of Classification Search
USPC ..... Plt./101, 102, 104, 108, 130, 132, 141, Plt./143
See application file for complete search history.

(56) References Cited

PUBLICATIONS

HelpMeFind Roses, Clematis and Peonies. https://www.helpmefind.com/gardening/l.php?l=2.69116. citation for Kortuberlou. retrieved Oct. 10, 2017. 1 page.*
World Federation of Roses Societies website. http://www.worldrose.org/trials/2014/lyon/lyon10.asp. retrieved Oct. 11, 2017. 1 page.*

* cited by examiner

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

'KORtuberlou' is a new and distinct variety of *Rosa hybrida* which is characterized by the combination of an upright growth habit, a moderately vigorous rate of growth, panicles bearing five to nine yellow flowers which are margined pink, double flowers with light fragrance, and excellent resistance to common rose diseases. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORtuberlou'.

STATEMENT REGARDING PRIOR DISCLOSURES BY THE INVENTOR UNDER 37 C.F.R. 1.77(B)(6)

The first public disclosure of the claimed plant was made in Germany, in the inventor's retail catalog, first mailed on Sep. 1, 2015. 'KORtuberlou' was not publically available or sold prior to one year before the date of the instant application.

BACKGROUND OF THE INVENTION

Parentage: The *Rosa hybrida* variety 'KORtuberlou' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth habit and uniform flowering; and
2. Abundant, recurrent yellow flowers that are margined pink; and 3. Attractive and abundant foliage; and
4. Resistance to diseases encountered in landscapes and gardens.

This combination of qualities is not present in prior rose cultivars known to the inventor. These objectives have been substantially achieved and in that distinguish 'KORtuberlou' from all other varieties known to the inventor.

'KORtuberlou' is a seedling selection which resulted from the controlled pollination of *Rosa hybrida* 'KORquelda' (U.S. Plant Pat. No. 17,048), the seed parent, and with an unnamed *Rosa hybrida* seedling (unpatented) developed and owned by the same inventor, the pollen parent, during the summer of 2002. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2003 from the seedling beds due to its superior characteristics and asexually propagated for further evaluation. This new and distinctive rose variety was given the name 'KORtuberlou'.

Asexual Reproduction: 'KORtuberlou' was first asexually propagated by bud grafting in July of 2003 at the inventor's nursery in Klein Offenseth-Sparrieshoop, Germany. Subsequently, 'KORtuberlou' has been successfully propagated by stem cuttings and bud grafting in Jackson County, Oreg. These initial and other subsequent propagations conducted in controlled environments demonstrate that 'KORtuberlou' reproduces true to type in successive generations of asexual reproduction.

SUMMARY OF THE INVENTION

The following characteristics have been repeatedly observed and represent the distinguishing characteristics of the new *Rosa hybrida* cultivar 'KORtuberlou'. These traits, in combination, distinguish 'KORtuberlou' as a new and distinct cultivar.

1. *Rosa hybrida* 'KORtuberlou' exhibits a moderately vigorous growth rate; and
2. *Rosa hybrida* 'KORtuberlou' exhibits an upright growth habit; and
3. *Rosa hybrida* 'KORtuberlou' exhibits panicles bearing five to nine yellow flowers which are margined pink; and
4. *Rosa hybrida* 'KORtuberlou' exhibits small, double flowers with a light sweet, fruity fragrance; and
5. *Rosa hybrida* 'KORtuberlou' exhibits excellent resistance to rust, black spot disease, *Botrytis* and powdery mildew.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORtuberlou', taken from a three year old plant.

DETAILED BOTANICAL DESCRIPTION

The following is a detailed botanical description of a new and distinct variety of *Rosa hybrida* known as 'KORtuberlou', based upon observations made in June of 2016 from three year old, field-grown plants in Jackson County, Oreg. Those skilled in the art will appreciate that certain characteristics will vary with older or, conversely, with younger plants. 'KORtuberlou' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2001 edition except where common terms of color are used.

A botanical description of 'KORtuberlou' and comparisons with the parents and closest known comparator variety of *Rosa hybrida* are provided below.

General plant description:

*Growth rate.*—Moderately vigorous.

*Growth habit.*—Upright.

*Mature dimensions.*—100 cm tall and 50 cm wide, on average.

*Cold hardiness.*—Grown successfully in USDA Hardiness Zones 5 through 9.

*Propagation.*—Stem cuttings and bud grafting.

*Disease resistance.*—Excellent resistance to powdery mildew (*Sphaerotheca pannosa*), blackspot (*Diplocarpon rosae*), rust (*Phragmidium* sp.) and *Botrytis* diseases under normal growing conditions in Jackson County, Oreg.

Root system:

*Type.*—Fibrous root system.

*Branching.*—Freely branched.

*Density.*—Moderately dense.

*Color.*—Greyed-yellow Group 161D.

*Distribution.*—Roots distributed evenly throughout the soil profile, from shallow to deep.

Stems:

*Stem color.*—Young stems are Yellow-Green Group 146B; mature stems are Yellow-Green Group 146C.

*Anthocyanin intonations.*—Intonations of Greyed-Purple Group 183D are present on young stems.

*Stem surface texture.*—Both juvenile and mature stems are smooth.

*Stem dimensions.*—Typical mature stems are approximately 40 to 80 cm long and 6 to 12 mm in diameter.

*Prickles.*—Incidence — Typically 6 prickles per 10 cm of stem, on average. Size — Average length is 15 mm long. Immature prickle color — Greyed-Red Group 182A. Mature prickle color — Greyed-Red Group 183C. Shape — Convex. Texture — Smooth.

Leaves:

*Arrangement.*—Imparipinnate compound leaves; mature axillary leaves consisting of 7 leaflets.

*Attachment.*—Petiolate.

*Dimensions.*—170 mm long and 110 mm wide.

*Abundance.*—Average; approximately 120 leaves.

*Stipules.*—Size — 30 mm long and 12 mm wide. Stipule color — Yellow-Green Group 147C. Anthocyanin intonations — Greyed-Red Group 182C intonations are present on the center rib of the adaxial surface; intonations of Greyed-Red Group 183D are present on the abaxial surface. Stipitate glands — A limited number of stipitate glands are present. Margins — With stipitate glands. Texture, adaxial surfaces — Glabrous. Texture, abaxial surfaces — Glabrous. Apex — Apiculate. Base — Flat.

*Petiole.*—Length — Average of 15 mm. Diameter — Average of 3 mm. Petiole color, adaxial surface — Yellow-Green Group 146C. Petiole color, abaxial surface — Yellow-Green Group 146C. Anthocyanin intonations — Greyed-Red Group 182C intonations are present along the margins of the adaxial surface; light intonations are present on the abaxial surface. Margins — With scarce stipitate glands. Prickles — A few small prickles are present. Stipitate glands — Limited number of stipitate glands. Texture — Glabrous. Strength — Strong; stiff.

*Rachis.*—Length — Average 35 mm. Diameter — Average 2.5 mm. Color — Yellow-Green Group 146C. Anthocyanin intonations — Greyed-Red Group 182C intonations are present on the center rib of the adaxial surface. Margins — A few stipitate glands are present along the margins of the adaxial surface. Prickles — A few small prickles on the abaxial surface. Stipitate glands — A limited number of stipitate glands are present. Texture — Glabrous.

*Leaflets.*—Dimensions — Average size of the terminal leaflet is 60 mm long and 48 mm wide. Shape — Ovate. Apex — Cuspidate. Base — Obtuse.

Margins — Serrated; lightly undulated. Luster, texture and pubescence; adaxial surface — Semi-glossy, smooth and glabrous. Luster, texture and pubescence; abaxial surface — Matte, smooth and glabrous. Juvenile foliage color, adaxial surface — Green Group 137A. Juvenile foliage color, abaxial surface — Yellow-Green Group 147C. Mature foliage color, adaxial surface — Yellow-Green Group 147A. Mature foliage color, abaxial surface — Yellow-Green Group 147B. Anthocyanin intonations — Very strong intonations of Greyed-Red Group 178B are present along the margins of the abaxial surface. Venation — Reticulate. Petiolule — Dimensions — 2.0 mm long and 0.5 mm in diameter. Petiolule color, adaxial surface — Yellow-Green Group 146D. Petiolule color, abaxial surface — Yellow-Green Group 147C. Anthocyanin intonations — Greyed-Orange Group 177D. Prickles — None observed. Texture, adaxial and abaxial surfaces — Leathery. Margins — Occasional stipitate glands.

Inflorescence:

*Inflorescence type.*—Panicles which bear 5 to 9 flower buds. Flowers are held slightly pendant.

*Blooming habit.*—Recurrent; very floriferous.

*Size.*—175 mm tall and 170 mm wide, on average.

*Peduncle.*—Length — 60 to 180 mm average length. Diameter — 5.0 to 7.0 mm average diameter. Color — Yellow-Green Group 146B. Anthocyanin intonations — Very strong intonations of Greyed-Red Group 178A. Strength — Strong. Surface — Glabrous.

Flowering laterals: Present below the initiation of inflorescence. Generally 2 to 5 flowering laterals are present, with 1 to 5 flowers per flowering shoot.

Bud:

*Bud form.*—Long; pointed ovoid.

*Size.*—Upon opening, 30 mm in length from base of receptacle to distal end of bud and 15 mm diameter at its widest point.

*Texture.*—Smooth.

*Color, as sepals first unfold.*—Yellow Group 12B with intonations of Red Group 46B to 46C.

*Color when one-quarter open, inner side.*—Marginal zone — Yellow-Orange Group 16B with intonations of Red Group 46B. Middle zone — Yellow-Orange Group 16C. Basal zone — Yellow Group 7A.

*Color when one-quarter open, outer side.*—Marginal zone — Yellow-Orange Group 16B with intonations of Red Group 46B. Middle zone — Yellow-Orange Group 16B. Basal zone — Yellow Group 13C.

*Color, outermost petals.*—General tonality is Red Group 45C.

Flower:

*Pedicel.*—Length — 50 to 60 mm average length. Diameter — 2.0 to 4.0 mm average diameter. Color — Yellow-Green Group 146C. Anthocyanin intonations — Greyed-Red Group 178B. Strength — Somewhat strong. Surface — Smooth.

*Calyx.*—General — Comprised of five polysepalous sepals, with moderate foliaceous appendages present on three sepals. Diameter of calyx — 60 mm, at anthesis. Sepals — Color, upper surface — Yellow-Green Group 147C. Color, lower surface — Yellow-Green Group 146B. Anthocyanin intonations — Intonations of Greyed-Red Group 178B are present on the lower surface. Size — 25 to 30 mm long and 8 to 14 mm wide, on average. Apex — Cirrose. Base — Flat at union with receptacle. Quantity — Five. Upper surface — Pubescent. Lower surface — Smooth. Margins — With stipitate glands. Stipitate glands — A limited number of stipitate glands are present.

*Corolla.*—Habit; type — Double. General shape of corolla — Cup-open; shallow. Shape of corolla when viewed from the side — Upon opening, upper portion — Flat. Upon opening, lower portion — Flattened convex. Open flower, upper portion — Flat. Open flower, lower portion — Flattened convex. Dimensions — Medium size for a shrub rose. When open, the average flower diameter is 80 mm and the average flower height is 50 mm. Fragrance — Light fragrance; sweet, fruity. Duration — On the plant for 4 to 6 days. Senesced petals drop away cleanly. Petals — Petal count — Exhibits double flowers with 25 petals under normal conditions. Petal reflex — Petals are slightly reflexed. Timing of petal reflex — Simultaneous. Petal margin — Emarginate. Petal shape — Obovate. Apex — Obtuse. Base — Obtuse. Dimensions — 30 to 35 mm long and 25 to 40 mm wide. Texture, inner surface — Smooth. Texture, outer surface — Smooth. Petal color, upon opening — Outermost petals, inner surface — Marginal zone — Irregular coloring, ranging from Yellow Group 9C to Red Group 46B. Middle zone — Irregular coloring, ranging from Yellow Group 9C to Red Group 46B. Basal zone — Yellow Group 9B. Outermost petals, outer surface — Marginal zone — Yellow Group 4C, suffused with Red Group 46B. Middle zone — Yellow Group 4C, suffused with Red Group 46B. Basal zone — Yellow Group 9B. Innermost petals, inner surface — Yellow Group 13B and suffused with Red Group 46B to 46C at the marginal and middle zones. Innermost petals, outer surface — Yellow Group 13B and lightly suffused with Orange Group 24B at the marginal and middle zones. Basal petal spots, upon opening — No distinctive coloration at the petal base. Petal color, after opening — Outermost petals, inner surface — Marginal zone — Red-Purple Group 61C. Middle zone — Red Group 52C. Basal zone — Yellow Group 2B. Outermost petals, outer surface — Marginal zone — Red-Purple Group 61C. Middle zone — Red Group 52C. Basal zone — Yellow Group 2B. Innermost petals, inner surface — Marginal zone — Yellow Group 9B and suffused with Orange-Red Group 32B. Middle zone — Yellow Group 9B and suffused with Orange-Red Group 32B. Basal zone — Yellow-Orange Group 9B. Innermost petals, outer surface — Marginal zone — Yellow-Orange Group 16B. Middle zone — Yellow-Orange Group 16B and suffused with Orange Group 24C. Basal zone — Yellow-Orange Group 16B and suffused with Orange Group 24C. Basal petal spots, after opening — No distinctive coloration at the petal base. General Tonality — On open flower, the outer portion of the flower is Red Group 46C and the center is Orange Group 24C. No change in general tonality at the end of the fifth day; thereafter the general tonality is Yellow Group 10D, margined with Red Group 52C. Petaloids — Quantity — 8 petaloids per flower, on average. Dimensions — Approximately 10 to 25 mm long and 7 to 15 mm wide. Color, inner surface — Varied; typically Yellow Group 13B and occasionally suffused with Orange Group 25C. Color, outer surface — Varied; typically Yellow Group 14C and occasionally suffused with Orange Group 25D. Margins — Irregular; undulated to indented. Shape — Irregular; obovate to spatulate. Apex — Acute to obtuse. Base — Attenuate. Texture, inner and outer surfaces — Smooth.

Reproductive organs:

*Stamens.*—Quantity — Approximately 60, on average, arranged around the styles. Anthers — Shape — Reniform. Dimensions — 4.0 mm long and 2.0 mm wide, on average. Color — Yellow-Orange Group 16C. Pollen — Present; abundant. Color is Greyed-Orange Group 163B. Filaments — Color — Yellow Group 9B. Length — 6.0 mm.

*Pistils.*—Quantity — Approximately 40. Stigmas — Size — 1.0 mm. Location — Inferior in position to anthers. Color — Greyed-Orange Group 163B. Styles — Length — Approximately 5.0 mm long. Color — Yellow Group 2D with intonations of Red Group 46B.

*Ovary.*—Dimensions — 8.0 mm long and 6.0 mm in diameter. Color — Green-White Group 157C.

*Receptacle.*—Shape — Funnel-shaped. Dimensions — Approximately 10.0 mm high and 7.0 mm wide. Color — Yellow-Green Group 146C, with intonations of Greyed-Purple Group 187C. Texture — Smooth; glabrous.

Hips and seed formation: Not observed to date.

COMPARISONS WITH THE PARENTS

The new rose plant may be distinguished from its seed parent, *Rosa hybrida* 'KORquelda', by the characteristics described in Chart 1.

CHART 1

| Characteristic | 'KORtuberlou' | 'KORquelda' |
|---|---|---|
| Flower size. | Larger than 'KORquelda'. | Smaller than 'KORtuberlou'. |

CHART 1-continued

| Characteristic | 'KORtuberlou' | 'KORquelda' |
|---|---|---|
| Flower type; petal count. | Semi-double. | Very double. |
| Flower colon. | Yellow, with pink at marginal zones. | Yellow. |

The new rose plant may be distinguished from its pollen parent, an unnamed *Rosa hybrida* seedling, by the characteristics described in Chart 2.

CHART 2

| Characteristic | 'KORtuberlou' | Unnamed pollen parent |
|---|---|---|
| Growth habit. | Upright and freely branched. | Compact and not freely branched. |
| Disease resistance. | Excellent. | Average. |
| Flower type; petal count. | Semi-double. | Double. |

COMPARISON WITH THE MOST SIMILAR *ROSA* CULTIVAR KNOWN TO THE INVENTOR

For a comparison, several physical characteristics of the *Rosa hybrida* variety 'KORgohowa', a rose variety from the same inventor which is described and illustrated in U.S. Plant Pat. No. 22,539, are compared to 'KORtuberlou' in Chart 3.

CHART 3

| Characteristic | 'KORtuberlou' | 'KORgohowa' |
|---|---|---|
| Leaf size. | 170 mm long and 120 mm wide. | 150 mm long and 120 mm wide. |
| Petal count. | 25. | 50 to 60. |
| Shape of prickles on stems. | Convex. | Linear. |

That which is claimed is:

1. A new and distinct variety of rose plant named 'KORtuberlou', as described and illustrated herein.

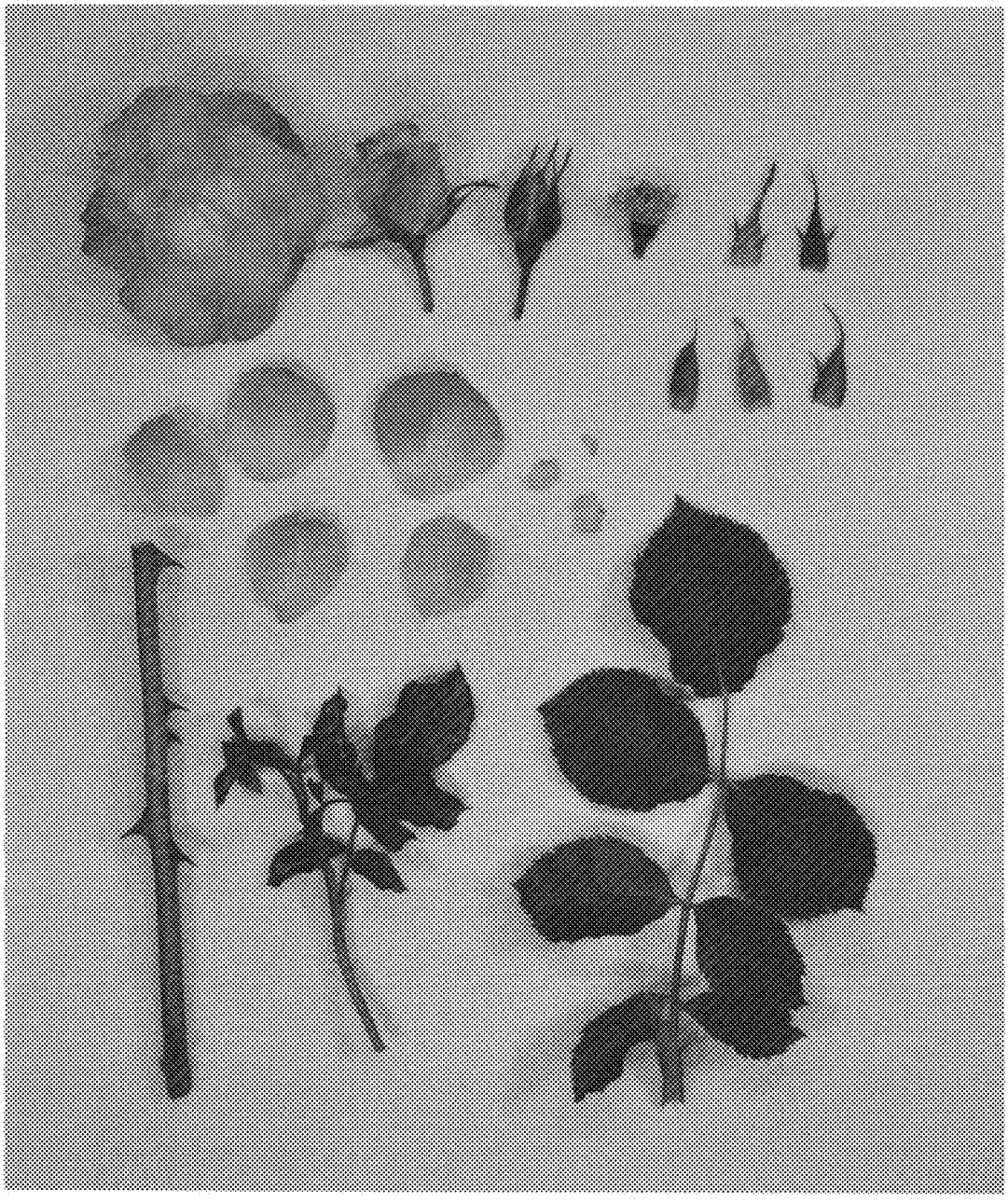

* * * * *